United States Patent [19]

Harris

[11] Patent Number: 4,529,726
[45] Date of Patent: Jul. 16, 1985

[54] PESTICIDAL NITROMETHYLENE DERIVATIVES

[75] Inventor: Martin Harris, Sittingbourne, England

[73] Assignee: Shell Oil Company, Houston, Tex.

[21] Appl. No.: 578,142

[22] Filed: Feb. 8, 1984

[30] Foreign Application Priority Data

Feb. 17, 1983 [GB] United Kingdom ............... 8304385
Sep. 23, 1983 [GB] United Kingdom ............... 8325538

[51] Int. Cl.³ ............... C07D 279/04; C07D 419/06; A01N 43/86
[52] U.S. Cl. ............................ 514/226; 544/54; 544/55
[58] Field of Search .................. 544/54, 55; 424/246

[56] References Cited

U.S. PATENT DOCUMENTS 4,052,388 10/1977 Powell .................................. 544/54

Primary Examiner—John M. Ford

[57] ABSTRACT

A 3-acyl-2-nitromethylene-tetrahydro-2H-1,3-thiazines of the general formula:

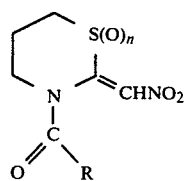

in which R represents an optionally ring-substituted benzyl group; a cycloalkyl group optionally substituted by halogen and/or alkyl; or an alkyl, alkenyl or alkynyl group of 2 or more carbon atoms optionally substituted by one or more of the same or different substituents selected from halogen, optionally substituted phenyl, phthalimido, alkoxy, haloalkoxy, alkoxyalkoxy, hydroxy, thiol, cycloalkyl optionally substituted by halogen and/or alkyl, and groups of the formula —COR¹, —X.CO.R¹ or —CO.X.R¹

5 Claims, No Drawings

PESTICIDAL NITROMETHYLENE DERIVATIVES

This invention relates to certain 3-acyl-2-nitromethylenetetrahydro-2H-1,3-thiazines, to a process for their preparation and to their use as pesticides, in particular against insect pests.

U.S. Patent Specification No. 4,052,388 describes the compound 3-acetyl-2-nitromethylene-tetrahydro-2H-1,3-thiazine and its insecticidal properties. It has now been found that other 3-acyl derivatives of 2-nitromethylene-tetrahydro-2H-1,3-thiazine also exhibit interesting pesticidal activity.

Accordingly the invention provides 3-acyl-2-nitromethylene-tetrahydro-2H-1,3-thiazines of the general formula:

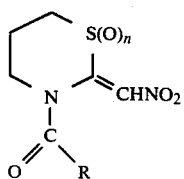

(I)

in which R represents an optionally ring-substituted benzyl group; a cycloalkyl group optionally substituted by halogen and/or alkyl; or an alkyl, alkenyl or alkynyl group of 2 or more carbon atoms optionally substituted by one or more of the same or different substituents selected from halogen, optionally substituted phenyl, phthalimido, alkoxy, haloalkoxy, alkoxyalkoxy, hydroxy, thiol, cycloalkyl optionally substituted by halogen and/or alkyl, and groups of the formula

—COR$^1$, —X.CO.R$^1$ or —CO.X.R$^1$ in which X represents oxygen or sulphur and R$^1$ represents hydrogen, optionally substituted phenyl, cycloalkyl optionally substituted by halogen and/or alkyl, and alkyl optionally substituted by one or more of the same or different substituents selected from halogen, alkoxy, haloalkoxy, and optionally substituted phenyl; and n is 0 or 1.

Throughout this Specification, except where otherwise stated, any alkyl, alkenyl or alkynyl moiety preferably has up to 6, especially up to 4, carbon atoms. In an optionally substituted phenyl moiety, the optional substituents are preferably selected from halogen atoms and alkyl, alkoxy, haloalkyl, haloalkoxy, cyano, nitro, amino, hydroxy and alkoxycarbonyl groups. Any cycloalkyl group preferably has 3 to 6 ring carbon atoms and is preferably unsubstituted or substituted by up to 4 chlorine atoms and/or methyl groups. Preferred halogen atoms are chlorine atoms.

Preferably R represents a benzyl group optionally ring-substituted by one or more halogen atoms and/or C(1-4) alkyl groups; an unsubstituted cycloalkyl group having 3 to 6 carbon atoms; or an alkyl, alkenyl or alkynyl group of 2 to 10 carbon atoms optionally substituted by one or more of the same or different substituents selected from halogen, phenyl optionally substituted by one or more halogen atoms and/or C(1-4) alkyl groups, phthalimido, C(1-4) alkoxy, C(1-4) haloalkoxy, hydroxy, thiol, unsubstituted C(3-6) cycloalkyl, and groups of the formula

—COR$^1$, —X.COR$^1$ or —CO.XR$^1$ in which X represents oxygen or sulphur and R$^1$ represents hydrogen, C(3-6) cycloalkyl, phenyl optionally substituted by halogen and/or C(1-4) alkyl, and C(1-6) alkyl optionally substituted by halogen, C(1-4) alkoxy, C(1-4) haloalkoxy and/or phenyl optionally substituted by halogen and/or C(1-4) alkyl.

More preferably R represents a benzyl or halobenzyl group; a cyclopropyl group; an alkenyl or alkynyl group having 2 to 6 carbon atoms; or an alkyl group of 2 to 8 carbon atoms optionally substituted by one or more of the same or different substituents selected from halogen, phthalimido, and groups of formula

—COR$^1$, —O.COR$^1$ or —CO.OR$^1$ in which R$^1$ represents hydrogen, C(3-6) cycloalkyl, or C(1-6) alkyl optionally substituted by halogen and/or C(1-4) alkoxy.

Thus typically R represents an alkyl group of 2 or more carbon atoms optionally substituted by a halogen atom and/or by a (halo)alkanoyl or alkoxycarbonyl group of up to 6 carbon atoms or by a phthalimido group; a benzyl group; or an alkenyl group of up to 6 carbon atoms. Preferred compounds of this type are those in which R represents an alkyl group of 2 to 8 carbon atoms optionally substituted by a chlorine atom and/or a (chloro)alkanoyl or alkoxycarbonyl group of 2 to 4 carbon atoms, for example ethyl, propyl, iso-butyl, pentyl, heptyl, chloroethyl, methoxycarbonylethyl, chloropropyl, butanoylpropyl or (chlorobutanoyl)-chloropropyl; a benzyl group; or an alkenyl group of up to 4 carbon atoms, for example, vinyl.

Preferably n is 0.

It will be appreciated that the compounds of formula I are capable of existing in different geometrically isomeric forms. The invention includes both the individual isomers and mixtures of such isomers.

The invention includes also a process for the preparation of the 3-acyl-2-nitromethylene-tetrahydro-2H-1,3-thiazines of formula I, which comprises reacting the compound of the formula:

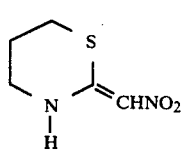

(II)

with a compound of the formula:

R—CO—Y (III)

in which R is as defined above in relation to formula I and Y represents a halogen, preferably chlorine, atom, or a group of formula —O.COR, in which R is as defined in relation to formula I, in the presence of a base, to produce a compound of the general formula I in which n is 0; and if desired, oxidising this compound to produce the corresponding compound of the general formula I in which n is 1. The base is preferably an organic base such as tertiary amine, for example a trialkylamine, triethylamine being particularly preferred. The reaction is preferably carried out at a temperature of 0° C. or below, for example, at a temperature from −30° C. to −10° C. The reaction is suitably carried out in an organic solvent, for example, a chlorinated hydrocarbon such as dichloromethane, or an amide such as dimethylformamide. The compounds of formula I in which n is 1 may be prepared by oxidising the corresponding derivative in which n is 0. This may be carried out using conventional oxidising agents, for example peracids such as m-chloroperbenzoic acid, or potassium hydrogen persulphate. Coveniently the derivative to be oxidised is dissolved in a suitable solvent, for example a chlorinated hydrogen solvent such as chloroform or dichlormethane, or a liquid alkanol such as ethanol.

As mentioned above, the 3-acyl-2-nitromethylene-tetrahydro-2H-1,3-thiazines of the invention are of interest as pesticides particularly against insect pests. They exhibit activity against such pests as the larval caterpillar or worm forms of insects, for example, of the genus Spodoptera and of the genus Heliothis. They are particularly useful for combating pests found in rice crops. For certain applications the combined physical and biological properties of the compounds of the invention are more advantageous than those of the known insecticide 3-acetyl-2-nitromethylene-tetrahydro-2H-1,3-thiazine.

Accordingly the invention includes pesticidal compositions comprising a 3-acyl-2-(nitromethylene)-tetrahydro-2H-1,3-thiazine of the invention together with a carrier.

Such a composition may contain a single compound or a mixture of several compounds of the invention. It is also envisaged that different isomers or mixtures of isomers may have different levels or spectra of activity and thus compositions may comprise individual isomers or mixtures of isomers. The invention further provides a method of combating pests, particular insect pests, at a locus, which comprises applying to the locus a pesticidally effective amount of compound or composition according to the present invention. An especially preferred locus is a paddy field bearing rice crops.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing $\frac{1}{2}$–10% w of active ingredient. Granules are usually prepared to have a size between 10 and 100 BS mesh (1.676–0.152 mm), and may be manufactured by agglomeration or impregnation techniques. Generally, granules will contain $\frac{1}{2}$–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension conentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

A composition of the invention may also contain other ingredients, for example, one or more other compounds possessing pesticidal, herbicidal or fungicidal properties, or attractants, for example pheromones or food ingredients, for use in baits and trap formulations.

It has also been found that the thermal stability of the compounds and compositions of the invention may be improved by the addition of stabilizing amounts, usually 10–100%w based on the compound, of certain organo nitrogen compounds such as urea, dialkylureas, thiourea or guanidine salts or alkali metal salts of weak acids such as bicarbonates, acetates or benzoates.

The invention is illustrated further in the following Examples.

EXAMPLE 1

(A)

3-Butanoyl-2-nitromethylene-tetrahydro-2H-1,3-thiazine (B)

3-(2-butanoylbutanoyl)-2-nitromethylene-tetrahydro-2H-1,3-thiazine

Butanoyl chloride (0.75 g) in dichloromethane (10 ml) was added dropwise over a period of 15 minutes to a solution of 2-nitromethylene-tetrahydro-2H-1,3-thiazine (1.0 g) and triethylamine (2 ml) in dichloromethane (10 ml) at −20° C. under nitrogen. The reaction mixture was allowed to warm to ambient temperature over a period of 20 minutes and was then washed with 2% aqueous hydrochloric acid. The organic phase was dried and the solvent was removed under reduced pressure. The residue was purified by chromatography on silica using 1.5% methanol in dichloromethane as eluent.

Product (A) was obtained, after trituration with diethyl ether, as a white crystalline solid, m.p. 83°–84° C.

Analysis Calculated for $C_9H_{14}O_2N_2S$ C 47.0%; H 6.1%; N 12.2% Found C 47.0%; H 5.9%; N 12.2%

Product (B) was obtained as minor product, m.p. 67°–69° C.

Analysis Calculated for $C_{13}H_{20}O_4N_2S$ C 52.0%, H 6.7%; N 9.3% Found C 52.1%; H 6.7%; N 9.5%

EXAMPLE 2

3-(Phenylacetyl)-2-nitromethylene-tetrahydro-2H-1,3-thiazine

To a solution of phenylacetyl chloride (4.8 g) in dry dichloromethane (30 ml) at −20° C. was added triethylamine (5.2 ml) over a period of 20 minutes, followed by 2-(nitromethylene)-tetrahydro-2H-1,3-thiazine (3.2 g) in dry dichloromethane (30 ml) over a period of 20 minutes. The reaction mixture was allowed to warm to ambient temperature with stirring over a period of 30 minutes and was then worked up in a similar manner to that described in Example 1 to yield the required product as a white crystalline solid m.p. 121°–122° C.

Analysis Calculated for $C_{13}H_{14}O_3N_2S$ C 56.1%; H 5.0%; N 10.1% Found C 55.9%; H 4.9%; N 10.0%

EXAMPLE 3(A)

3-Propionyl-2-nitromethylene-tetrahydro-2H-1,3-thiazine

Propionyl chloride (1.8 g) was added dropwise over a period of 15 minutes to a mixture of 2-(nitromethylene)-tetrahydro-2H-1,3-thiazine (2.0 g) and triethylamine (2.4 g) in dimethylformamide (8 ml) at −30° C. under nitrogen. The reaction mixture was stirred for a further period of 35 minutes at −25° C. and was then poured into 2% hydrochloric acid. The mixture was extracted with dichloromethane and the organic layer was washed with sodium chloride solution and dried ($Na_2SO_4$). The solvent was then removed under reduced pressure and the residue was purified by chromatography on silica gel using 1% methanol in dichloromethane as eluent to yield the required product as a yellow crystalline solid m.p. 84°–86° C.

Analysis Calculated for $C_8H_{12}O_3N_2S$ C 44.4%; H 5.6%; N 13.0% Found C 44.2%, H 5.3%, N 13.0%

EXAMPLE 3(B)

3-Propionyl-2-nitromethylene-tetrahydro-2H-1,3-thiazine (Alternative Procedure)

Propionic anhydride (1.0 g) was added dropwise over a period of 10 minutes to a solution of 2-nitromethylenetetrahydro-2H-1,3-thiazine (1.0 g) and triethylamine (1.5 g) at −20° C. under nitrogen. The mixture was allowed to warm to ambient temperature and stirred for a further three hours. The mixture was then washed with 2% hydrochloric acid and the organic phase was dried ($Na_2SO_4$). The solvent was then removed under reduced pressure and the residue obtained was purified by chromatography on silica gel using 1% methanol in dichloromethane as eluent to yield the required product as a yellow crystalline solid.

EXAMPLES 4–32

Further compounds were prepared using procedures similar to those of the preceeding Examples. These compounds are identified together with their melting points and analyses in Table A.

TABLE A

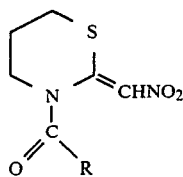

| Example | R | m.p. °C. | Analysis | C % | H % | N % |
|---|---|---|---|---|---|---|
| 4 | —(CH$_2$)$_3$Cl | 69–70 | Calc. for C$_9$H$_{13}$O$_3$N$_2$SCl | 40.8 | 4.9 | 10.6 |
| | | | Found | 40.6 | 5.0 | 10.5 |
| 5 | —(CH) (CH$_2$CH$_2$Cl)CO(CH$_2$)$_3$Cl | oil | Calc. for C$_{13}$H$_{18}$O$_4$N$_2$SCl$_2$ | 42.3 | 4.9 | 7.6 |
| | | | Found | 42.3 | 5.3 | 7.2 |
| 6 | —CH=CH$_2$ | 69 | Calc. for C$_8$H$_{10}$O$_3$N$_2$S | 44.9 | 4.7 | 13.1 |
| | | | Found | 45.2 | 4.7 | 13.1 |
| 7 | —(CH$_2$)$_6$CH$_3$ | 64–66 | Calc. for C$_{13}$H$_{22}$O$_3$N$_2$S | 54.6 | 7.7 | 9.8 |
| | | | Found | 54.8 | 7.8 | 9.9 |
| 8 | —(CH$_2$)$_2$COOCH$_3$ | 117–119 | Calc. for C$_{10}$H$_{14}$O$_5$N$_2$S | 43.8 | 5.1 | 10.2 |
| | | | Found | 43.9 | 5.1 | 10.2 |
| 9 | —(CH$_2$)$_3$COOCH$_3$ | 84–86 | Calc. for C$_{11}$H$_{16}$O$_5$N$_2$S | 45.8 | 5.6 | 9.7 |
| | | | Found | 46.3 | 5.8 | 9.8 |
| 10 | —CHClCH$_3$ | 88–90 | Calc. for C$_8$H$_{11}$O$_3$N$_2$S | 38.3 | 4.4 | 11.2 |
| | | | Found | 38.6 | 4.5 | 11.2 |
| 11 | —(CH$_2$)$_4$CH$_3$ | oil | Calc. for C$_{11}$H$_{18}$O$_3$N$_2$S | 51.2 | 7.0 | 10.9 |
| | | | Found | 51.6 | 7.0 | 10.2 |
| 12 | —CH$_2$CH(CH$_3$)$_2$ | 103–105 | Calc. for C$_{10}$H$_{16}$O$_3$N$_2$S | 49.2 | 6.6 | 11.5 |
| | | | Found | 48.9 | 6.3 | 11.2 |
| 13 | phthalimidopropyl | 125–127 | Calc. for C$_{17}$H$_{17}$N$_3$O$_5$S$_2$ | 54.4 | 4.5 | 11.2 |
| | | | Found | 53.3 | 4.3 | 10.7 |
| 14 | —CH$_2$CH$_2$CO$_2$C$_2$H$_5$ | 94–5 | Calc. for C$_{17}$H$_{16}$N$_2$O$_5$S | 45.8 | 5.6 | 9.7 |
| | | | Found | 45.9 | 5.6 | 9.7 |
| 15 | —(CH$_2$)$_2$CO$_2$iC$_3$H$_7$ | 99–100 | Calc. | 47.7 | 6.0 | 9.3 |
| | | | Found | 47.7 | 5.9 | 9.1 |
| 16 | —(CH$_2$)$_2$CO$_2$nC$_4$H$_9$ | 80–81 | Calc. | 49.4 | 6.3 | 8.9 |
| | | | Found | 49.1 | 6.4 | 8.6 |
| 17 | —(CH$_2$)$_4$Br | 64–66 | Calc. | 37.2 | 4.6 | 8.7 |
| | | | Found | 37.3 | 4.6 | 8.7 |
| 18 | —CH.CO(CH$_2$)$_4$Br<br>\|<br>(CH$_2$)$_3$Br | 70–72 | Calc. | 37.0 | 4.5 | 5.8 |
| | | | Found | 37.5 | 4.5 | 5.9 |
| 19 | —(CH$_2$)$_4$O.CO.CH$_3$ | oil | Calc. | 47.7 | 6.0 | 9.3 |
| | | | Found | 48.3 | 6.3 | 8.4 |
| 20 | —(CH$_2$)$_3$I | 90–92 | Calc. | 30.3 | 3.7 | 7.9 |
| | | | Found | 31.1 | 3.9 | 8.0 |
| 21 | —(CH$_2$)$_3$Br | 93–95 | Calc. | 35.0 | 4.2 | 9.1 |
| | | | Found | 35.3 | 4.1 | 9.1 |
| 22 | —(CH$_2$)$_2$CO$_2$cyclohexyl | 87–89 | Calc. | 52.6 | 6.4 | 8.2 |
| | | | Found | 53.0 | 6.8 | 8.3 |
| 23 | —(CH$_2$)$_2$CO$_2$(CH$_2$)$_2$OC$_2$H$_5$ | 69–71 | Calc. | 47.0 | 6.0 | 8.4 |
| | | | Found | 47.0 | 6.3 | 8.4 |
| 24 | —CH$_2$(4-chlorophenyl) | 117 | Calc. | 49.9 | 4.2 | 9.0 |
| | | | Found | 50.0 | 4.3 | 9.0 |
| 25 | —(CH$_2$)$_4$O.CHO | 64–66 | Calc. | 45.8 | 5.6 | 9.7 |
| | | | Found | 45.4 | 5.5 | 10.2 |
| 26 | Cyclopropyl | 103–105 | Calc. | 47.4 | 5.3 | 12.3 |
| | | | Found | 47.2 | 5.5 | 12.3 |
| 27 | —(CH$_2$)$_3$O.CO.CH$_3$ | oil | Calc. | 45.8 | 5.6 | 9.7 |
| | | | Found | 45.5 | 5.4 | 10.5 |
| 28 | —(CH$_2$)$_3$O.CHO | 82–84 | Calc. | 43.8 | 5.1 | 10.2 |
| | | | Found | 43.5 | 5.3 | 10.6 |
| 29 | —CH(CH$_2$)$_3$CH$_3$<br>\|<br>C(O)(CH$_2$)$_3$CH$_3$ | 67–70 | Calc. | 57.3 | 7.8 | 7.9 |
| | | | Found | 56.4 | 8.0 | 8.0 |
| 30 | —CH.CH.(CH$_3$)$_2$<br>\|<br>C(O).CH$_2$.CH(CH$_3$)$_2$ | oil | Calc. | 54.9 | 7.3 | 8.5 |
| | | | Found | 55.0 | 7.2 | 8.6 |
| 31 | —(CH$_2$)$_8$CH=CH$_2$ | oil | Calc. | 58.6 | 8.4 | 8.5 |
| | | | Found | 58.9 | 8.0 | 8.6 |
| 32 | —(CH$_2$)$_8$C≡CH | oil | Analysed by NMR: chemical shift (δ, ppm relative to tetramethylsilane in CDCl$_3$) of the =CH.NO$_2$ proton: 7.2(singlet). | | | |

EXAMPLE 33

Preparation of the S-oxide of the compound of Example 8

2.0 g of m-chloroperbenzoic acid dissolved in 60 mls dichloromethane were added dropwise to a solution of 2.0 g of the compound of Example 8 in 100 mls dichloromethane, with stirring, at $-15°$ C., over 30 minutes. The mixture was then allowed to warm to room temperature and stirred for 1½ hours. 6 g sodium carbonate were then added, followed by stirring for a further 20 minutes. The mixture was then filtered, the solvent removed under reduced pressure, and the residue purified by column chromatography over silica. 1.1 g of the desired compound was obtained as an oil.

| Analysis | C | H | N |
|---|---|---|---|
| Calculated for $C_9H_{15}NO_4S$ | 39.6 | 4.7 | 8.6 |
| Found | 41.4 | 4.8 | 9.7 |

EXAMPLE 34

Pesticidal Activity

The presticidal activity of the compounds of the invention was assessed against the following insect pests.
*Spodoptera littoralis* (S.l.)
*Aedes aegypti* (A.a)
*Musca domestica* (M.d.)
*Alphis fabae* (A.f.)

The test methods employed for each species appear below; in each test, unless otherwise stated, a 0.2% solution or suspension of each test compound in 16.7% acetone in water containing 0.04% Triton X-100 (Trade Mark) was sprayed onto the test species; controls were sprayed with a control solution of water, acetone and Triton X-100 (Trade Mark) in the same proportions. The tests were all conducted under normal insectary conditions 23° C.±2° C. (fluctuating light and humidity).

(i) *Spodoptera littoralis* (S.l.)

Second instar larvae were used in the tests. Each test solution and the control solution was sprayed onto a separate petri dish containing a nutrious diet on which the *Spodoptera littoralis* larvae had been reared.

When the spray deposit had dried each dish was infested with 10 2nd instar larvae. Mortality assessments were made 1 and 7 days after spraying and the percentage mortality calculated.

(ii) *Aedes aegypti* (A.a.)

Early 4th instar larvae were used in the tests. Test solutions were made up to 3 ppm of active ingredient in water containing 0.04% Triton X-100 (Trade Mark); acetone was initially present to aid solution, but was subsequently allowed to evaporate off.

Ten early 4th instar larvae were placed in 100 ml of the test solution. After 48 hours, larval mortality (as a percentage) was recorded.

Any surviving larvae were then fed with a small quantity of animal feed pellets and the final percentage mortality of adults and pupae made when all the larvae had either pupated and turned into adults, or died.

(iii) *Musca domestica* (M.d.)

Batches of ten 2 to 3 day old milk-fed adult female houseflies (*Musca domestica*) anaesthetized using carbon dioxide were placed on petri dishes lined with filter paper. The dishes were sprayed with the test formulations using a spray machine operating on a logarithmic dilution principle. The flies were subsequently retained in the petri dishes and were fed with a dilute milk solution which was dripped down the side of the petri dish and absorbed onto the filter paper. Mortality was assessed after 24 hours.

(iv) *Aphis fabae* (A.f.)

Tests were carried out on adult black bean aphids (*Aphis fabae*). Pairs of broad bean leaves on filter paper in petri dishes were sprayed side by side with uncounted quantities of aphids in small gauze-covered containers. After passing through the spray the aphids were tipped onto the leaves and lids were placed on the petri dishes. Mortality was assessed after 24 hours.

The results of these tests are shown in Table B in which the test species are identified by the initials noted above and the activity of each compound is expressed in terms of the percentage mortality:
A denotes 90–100% mortality
B denotes 50–80% mortality
C denotes 0–40% mortality.

TABLE B

| Compound of Example No. | Insecticidal Activity | | | | | |
|---|---|---|---|---|---|---|
| | S.l. | | A.a. | | | |
| | 1 day | 7 days | 2 days | Final | M.d. | A.f. |
| 1 A | A | A | C | A | A | A |
| 1 B | A | A | C | A | A | A |
| 4 | A | A | C | A | A | A |
| 5 | A | A | C | A | A | C |
| 6 | A | A | C | C | A | A |
| 7 | A | A | A | A | A | A |
| 8 | A | A | B | A | A | A |
| 9 | B | A | C | A | A | A |
| 10 | B | B | C | B | B | B |
| 2 | A | A | B | B | B | B |
| 11 | A | A | C | C | A | A |
| 12 | A | A | A | A | A | A |
| 13 | C | A | C | A | A | C |
| 14 | A | A | B | A | A | A |
| 3 | A | A | A | A | A | A |
| 15 | A | A | C | A | A | A |
| 16 | A | A | A | A | A | A |
| 17 | A | A | A | A | A | A |
| 18 | A | A | A | A | A | A |
| 19 | A | A | A | A | A | C |
| 20 | A | A | B | A | A | A |
| 21 | A | A | B | A | A | A |
| 22 | A | A | A | A | A | C |
| 23 | A | A | A | A | A | C |
| 24 | A | A | C | A | A | A |
| 25 | A | A | B | A | A | A |
| 26 | A | A | B | A | A | A |
| 27 | A | A | B | A | A | A |
| 28 | A | A | C | A | A | A |
| 31 | A | A | B | A | A | A |
| 33 | A | A | A | A | A | B |

EXAMPLE 35

Determination of Toxicity Index

The toxicities of compounds according to the invention relative to a standard insecticide, Parathion, against corn earworm larvae (*Heliothis zea*) were tested by spraying a broad bean plant with aqueous dilutions of an acetone solution of test compound containing an emulsifier. Immediately after spraying, 5 larvae were transferred to the plant and held for 44–46 hours, at which time the dead and moribund larvae were counted. The tests were conducted employing several different dosage rates for each test compound.

In each instance, the toxicity of the compound of the invention was compared to that of a standard pesticide, Parathion, the relative toxicity then being expressed in terms of the relationship between the amount of compound of the invention and the amount of the standard pesticide required to produce 50% mortality of the test insect. The standard pesticide is given an arbitrary Toxicity Index of 100. Thus a test compound having a Toxicity Index of 50 would be half as active, while one having a Toxicity Index of 200 would be twice as active, as the standard pesticide. The Toxicity Indices measured are given in Table C.

TABLE C

| Compound of Example No. | Toxicity Index relative to Parathion = 100 |
|---|---|
| 1A | 1097 |
| 1B | |
| 2 | 1000 |
| 3 | 1500 |
| 4 | 1500 |
| 6 | 1500 |
| 8 | 1547 |
| 9 | 1000 |
| 11 | 1000 |
| 15 | 2500 |
| 16 | 4500 |
| 22 | 1500 |
| 23 | 1500 |
| 24 | 2677 |

For comparison purposes, the prior art compound 3-acetyl-2-nitromethylene-2H-1,3-thiazine (U.S. Pat. No. 4,052,388) was also tested. Its Toxicity Index relative to Parathion was 622.

I claim:

1. A compound of the formula

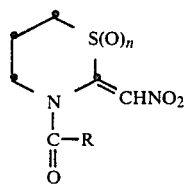

wherein n is zero or one, and R is
   (a) a benzyl group optionally substituted on the ring by halogen and/or alkyl of one to four carbon atoms;
   (b) a cycloalkyl group of three to six carbon atoms optionally substituted by halogen and/or alkyl of one to four carbon atoms;
   (c) an alkyl, alkenyl or alkynyl group of two to ten carbon atoms, optionally substituted by:
      (i) one or more halogen atoms;
      (ii) a phenyl group optionally substituted by one or more halogen atoms or by cyano, nitro, amino, hydroxy, or alkyl, alkoxy, haloalkyl, haloalkoxy or alkoxycarbonyl wherein each alkyl moiety contains from one to four carbon atoms;
      (iii) phthalimido;
      (iv) an alkoxy, alkylthio, alkoxyalkoxy or haloalkoxy group wherein each alkyl moiety contains from one to four carbon atoms;
      (v) hydroxy, mercapto;
      (vi) an optionally substituted cycloalkyl group as defined in (b) above.
      (vii) one of the groups $-C(O)R_1$, $-X-C(O)R^1$, or $-C(O)-XR^1$, wherein X is oxygen or sulfur and $R^1$ is hydrogen, optionally substituted phenyl as defined in (ii) above; optionally substituted cycloalkyl as defined in (b) above; or alkyl of one to four carbon atoms optionally substituted by halogen, alkoxy and/or haloalkyloxy of one to four carbon atoms; or optionally substituted phenyl as defined in (ii) above.

2. A compound as defined in claim 1 wherein n is zero, and R is:
   (a) a benzyl group optionally substituted on the ring by one or more halogen atoms and/or alkyl groups of one to four carbon atoms;
   (b) a cycloalkyl group of three to six carbon atoms;
   (c) an alkyl, alkenyl or alkynyl group of two to ten carbon atoms optionally substituted by
      (i) one or more halogen atoms;
      (ii) a phenyl group optionally substituted by one or more halogen atoms and/or alkyl groups of one to four carbon atoms;
      (iii) an alkoxy or haloalkoxy group of one to four carbon atoms;
      (iv) hydroxy or mercapto;
      (v) a cycloalkyl group of from three to six carbon atoms;
      (vi) one of the groups $-C(O)R^1$, $-X-C(O)R^1$ or $-C(O)X-R^1$, wherein $R^1$ is hydrogen, cycloalkyl of three to six carbon atoms; phenyl optionally substituted by halogen and/or alkyl of one to four carbon atoms; alkyl of one to six carbon atoms optionally substituted by halogen, alkoxy or haloalkoxy of one to four carbon atoms or phenyl optionally substituted by halogen and/or alkyl of one to four carbon atoms.

3. A compound as defined in claim 2 wherein n is zero, and R is benzyl optionally substituted by halogen; cyclopropyl; alkyl or haloalkyl of two to eight carbon atoms; alkenyl or alkynyl of two to six carbon atoms; or a group of the formula $-C(O)R^1$, $-O-C(O)R^1$ OR$-C(O)OR^1$ wherein $R^1$ is hydrogen, cycloalkyl of three to six carbon atoms or alkyl of one to six carbon atoms optionally substituted by halogen and/or alkoxy of from one to four carbon atoms.

4. A method for protecting a locus from unwanted insects, that comprises applying to the locus to be protected an effective dosage of a compound of claim 1.

5. An insecticidal composition, that comprises an effective amount of a compound of claim 1 together with an inert carrier, optionally a surface-active agent.

* * * * *